United States Patent
Messenger et al.

(10) Patent No.: US 9,538,959 B2
(45) Date of Patent: Jan. 10, 2017

(54) SYSTEM AND METHOD FOR HUMAN MONITORING

(71) Applicant: MORPHEUS, LLC, Cambridge, MA (US)

(72) Inventors: Stephen Messenger, Cambridge, MA (US); Julien de Wit, Cambridge, MA (US)

(73) Assignee: MORPHEUS, LLC, Cambridge, MA (US)

( * ) Notice: Subject to any disclaimer, the term of this patent is extended or adjusted under 35 U.S.C. 154(b) by 13 days.

(21) Appl. No.: 14/802,325

(22) Filed: Jul. 17, 2015

(65) Prior Publication Data

US 2016/0035205 A1    Feb. 4, 2016

Related U.S. Application Data

(60) Provisional application No. 62/032,595, filed on Aug. 3, 2014.

(51) Int. Cl.
G08B 1/08     (2006.01)
A61B 5/00     (2006.01)
(Continued)

(52) U.S. Cl.
CPC ............. *A61B 5/6887* (2013.01); *A61B 5/002* (2013.01); *A61B 5/681* (2013.01); *A61B 5/746* (2013.01);
(Continued)

(58) Field of Classification Search
CPC ............ G08B 21/0202; G08B 21/0208; G08B 21/0453
(Continued)

(56) References Cited

U.S. PATENT DOCUMENTS 5,512,880 A    4/1996   Abrams et al.
6,043,747 A    3/2000   Altenhofen
(Continued)

FOREIGN PATENT DOCUMENTS

CN    103268100 A    5/2013
CN    104224114 A    12/2014
WO    WO2013093686 A1    6/2013

OTHER PUBLICATIONS

ISR, ISA/US, Oct. 13, 2015.

*Primary Examiner* — Toan N Pham
(74) *Attorney, Agent, or Firm* — AKC Patents LLC; Aliki K. Collins

(57) ABSTRACT

A system for monitoring a user includes a transmitter positioned in a first location, a sensor system, first and second monitoring devices, a controller and an application. The sensor system collects data including sound and image data of the user, the user's vital data, and ambient condition data and transmits the collected data wirelessly to the transmitter. The first and second monitoring devices communicate wirelessly with the transmitter and are worn by first and second caregivers of the user, respectively, that are located in a second location that is different from the first location. The controller is located in the second location and communicates wirelessly with the first and second monitoring devices and the transmitter. The transmitter transmits wirelessly live data feeds to the first and second monitoring devices and to the controller and the live data feeds include the sound and image data of the user and the user's vital data. The application includes an analyzer that analyzes the live data feeds and determines whether any of the collected data has a value above a predetermined threshold or out of a predetermined range and sends an alarm notification to at least one of the first and second monitoring devices in cases when at least one of the collected data has a value above a predetermined threshold or out of a predetermined range.

20 Claims, 10 Drawing Sheets

(51) Int. Cl.
  *G08B 21/02* (2006.01)
  *G08B 21/04* (2006.01)
  *G06F 19/00* (2011.01)

(52) U.S. Cl.
  CPC ......... *G06F 19/345* (2013.01); *G06F 19/3418* (2013.01); *G08B 21/0208* (2013.01); *G08B 21/0453* (2013.01); *G08B 21/0492* (2013.01); *G06F 19/3487* (2013.01)

(58) Field of Classification Search
  USPC . 340/539.15, 539.1, 573.1, 539.12; 600/529, 600/549, 533
  See application file for complete search history.

(56) References Cited

U.S. PATENT DOCUMENTS

| | | | |
|---|---|---|---|
| 7,009,520 B2 | 3/2006 | Thompson | |
| 7,342,491 B2 | 3/2008 | Fujisawa et al. | |
| 7,407,484 B2 | 8/2008 | Korman | |
| 8,185,191 B1* | 5/2012 | Shapiro | A61B 5/0006 600/500 |
| 8,653,965 B1 | 2/2014 | Otto et al. | |
| 9,277,870 B2* | 3/2016 | Spolin | A61B 5/7275 |
| 2002/0135485 A1 | 9/2002 | Arakawa | |
| 2003/0149598 A1 | 8/2003 | Santoso et al. | |
| 2004/0246136 A1 | 12/2004 | Sanoner et al. | |
| 2005/0245839 A1* | 11/2005 | Stivoric | G06F 19/3418 600/549 |
| 2010/0007486 A1 | 1/2010 | Lu | |
| 2010/0217158 A1 | 8/2010 | Wolfe et al. | |
| 2010/0280500 A1 | 11/2010 | Skelton et al. | |
| 2011/0267196 A1 | 11/2011 | Hu et al. | |
| 2012/0032797 A1 | 2/2012 | Babineau | |
| 2012/0326875 A1 | 12/2012 | Coppola | |
| 2013/0342693 A1 | 12/2013 | Lee | |
| 2014/0055263 A1 | 2/2014 | Witt et al. | |
| 2014/0132413 A1 | 5/2014 | Covidien | |
| 2015/0094544 A1 | 4/2015 | Spolin et al. | |
| 2015/0100245 A1 | 4/2015 | Huang et al. | |

* cited by examiner

SYSTEM AND METHOD FOR HUMAN MONITORING

CROSS REFERENCE TO RELATED CO-PENDING APPLICATIONS

This application claims the benefit of U.S. provisional application Ser. No. 62/032,595 filed on Aug. 3, 2014 and entitled SYSTEM AND METHOD FOR HUMAN MONITORING, which is commonly assigned and the contents of which are expressly incorporated herein by reference.

FIELD OF THE INVENTION

The present invention relates to human monitoring systems and methods, and in particular to a system and method for monitoring a person that can send an alarm to alert only one of two caregivers when the person wakes up so that the other caregiver can continue to sleep.

BACKGROUND OF THE INVENTION

Parents and other caregivers often use a remote baby monitoring system for monitoring a baby, usually when it sleeps. The baby monitoring system usually includes sound and video recording devices for picking up sounds and images of the sleeping baby. The system also includes a loudspeaker providing an alarm to alert the parents when the baby cries, moves or wakes up. However, at night often both of the sleeping parents of the baby are woken up by the alarm, and thus they can not sleep well.

Accordingly, there is a need for a baby monitoring system that can send an alarm to alert only one of the parents so that other parent can continue to sleep.

SUMMARY OF THE INVENTION

In general, in one aspect, the invention features a system for monitoring a user including a transmitter, a sensor system, first and second monitoring devices, a controller and an application. The transmitter positioned in a first location in the vicinity of the user. The sensor system is configured to collect data including sound and image data of the user, the user's vital data, and ambient condition data, and to transmit the collected data wirelessly to the transmitter. The first and second monitoring devices are configured to communicate wirelessly with the transmitter and to be worn by first and second caregivers of the user, respectively. The first and second caregivers are located in a second location that is different from the first location. The controller is located in the second location and is configured to communicate wirelessly with the first and second monitoring devices and the transmitter. The transmitter is configured to transmit wirelessly live data feeds to the first and second monitoring devices and to the controller and the live data feeds include the sound and image data of the user and the user's vital data. The application includes an analyzer configured to analyze the live data feeds and to determine whether any of the collected data has a value above a predetermined threshold or out of a predetermined range and to send an alarm notification to at least one of the first and second monitoring devices in cases when at least one of the collected data has a value above a predetermined threshold or out of a predetermined range.

Implementations of this aspect of the invention may include one or more of the following features. The system further includes outside servers configured to receive wirelessly the live data feeds from the transmitter and to transmit wirelessly the live data feeds to the controller and the first and second monitoring devices. The application further includes a scheduler configured to schedule times when the first and second caregivers are on-duty and off-duty for receiving and responding to the alarm notifications. The application further includes a cry analyzer configured to analyze the sound data of the user and to determine whether the user is crying and to provide possible causes for the user's crying and to assign probabilities for such possible causes. The analyzer is further configured to analyze the live data feeds and to determine whether the user is about to require attention and to send a notification to at least one of the caregivers prior to the user waking up or crying. The application is further configured to receive the first and second caregiver's vital data, sleep pattern data and activity data and the analyzer is further configured to analyze the first and second caregiver's vital data, sleep pattern data, and activity data. The application is further configured to determine which caregiver is to receive the notification based on the analysis results of the first and second caregiver's vital data, sleep pattern data, and activity data. The application further includes a report generator configured to report and display the collected sound and image data of the user and the user's vital data versus time. Each of the first and second monitoring devices includes a vibrator for providing a vibrating alarm notification to at least one of the first and second caregivers indicating that one of the collected data has a value above a predetermined threshold or out of a predetermined range. Each of the first and second monitoring devices includes a vibrator and a speaker for providing a vibrating alarm and a sound alarm notification, respectively, to at least one of the first and second caregivers indicating that one of the collected data has a value above a predetermined threshold or out of a predetermined range and the vibrating alarm and the sound alarm comprise random patterns of vibrations and random patterns of sounds, respectively, and the random patterns of vibrations and random patterns of sounds are configured to bypass the caregiver's conditioned and expected patterns of vibrations and sounds, respectively. Each of the first and second monitoring devices further includes a speaker for providing a sound alarm notification to at least one of the first and second caregivers indicating that one of the collected data has a value above a predetermined threshold or out of a predetermined range. Each of the first and second monitoring devices further includes a microphone for capturing a voice signal of at least one of the caregivers and transmitting the voice signal to the user wirelessly via the transmitter. Each of the first and second monitoring devices further includes sensors configured to monitor each of the first and second caregiver's vital data, sleep pattern data and activity data. The sensor system includes wearable sensors configured to be worn by the user and to sense the user's vital data. The sensor system includes a daytime wearable sensor and a nighttime wearable sensor and the daytime wearable sensor and the nighttime wearable sensors are configured to be worn by the user and to sense the user's vital data during the day and during the night, respectively. The sensor system includes skin attachable sensors configured to be attached to the user's skin and to sense the user's vital data. The sensor system includes a microphone and a camera for capturing the sound and image data of the user, respectively. The sensor system is further configured to send an alarm notification to at least one of the first and second monitoring devices in cases when at least one of the collected data has a value above a predetermined threshold or out of a predetermined range. The sensor system is further configured to send an alarm notification to at least one of the first and second monitoring devices in cases when the user is about to or has moved away from the first location.

In general, in another aspect, the invention features a method for monitoring a user including the following steps. First, collecting data comprising sound and image data of the user, the user's vital data, and ambient condition data, via a sensor system and transmitting the collected data wirelessly to a transmitter positioned in a first location in the vicinity of the user. Next, providing first and second monitoring devices configured to communicate wirelessly with the transmitter and to be worn by first and second caregivers of the user, respectively. The first and second caregivers are located in a second location that is different from the first location. Next, providing a controller located in the second location and configured to communicate wirelessly with the first and second monitoring devices and the transmitter. Next, transmitting wirelessly live data feeds from the transmitter to the first and second monitoring devices and to the controller. The live data feeds include the sound and image data of the user and the user's vital data. Next, providing and application and analyzing the live data feeds and determining whether any of the collected data has a value above a predetermined threshold or out of a predetermined range with the application and sending an alarm notification to at least one of the first and second monitoring devices in cases when at least one of the collected data has a value above a predetermined threshold or out of a predetermined range.

Among the advantages of the invention, one or more of the following are included. During nighttime, this unique baby monitoring system wakes only one parent or caregiver that is on-duty, thereby allowing the other off-duty parent to continue sleeping. The invention relies initially on vibration to notify the on-duty parent, which has the advantage that it can awake solely and smoothly only the on-duty parent. Both the on-duty and the off-duty parents wear wristband devices such that a robust system of alerts is implemented. If the on-duty parent does not respond to the notification, then the off-duty parent receives the notification. Two-way communication exists between all system components and thereby the caregiver can hear and talk to the baby and the robustness of the system is increased. A change of the system parameters in one component of the system is reflected in all other system components. For parents who desire to use this system for monitoring multiple children, the system is easily scalable and expandable through additional components placed near or on those other children. The invention distinguishes between the different children and notifies parents accordingly. In addition to the baby monitor aspects, the invention monitors the sleep cycles of both the parents and the children, and the fitness/activity levels of the parents and children. The invention analyzes the sleep cycle state of the parents/caregivers to determine which parent/caregiver shall be awoken based on where the parent/caregiver is in their sleep cycle. A realization of this invention is that the parent/caregiver who is in the lighter parts of their sleep cycle will be awoken. The invention analyzes the sleep cycle of the baby to wake the parents prior to the baby reaching a high-stress state. The invention acts as a notification and response system for incoming telephone calls, emails, text messages, notifications from other phone applications, such as Facebook, Twitter, Whatsapp, Skype, CNN, among others. In these cases, the parents/caregivers are first notified of the incoming transmissions and then given the option to respond to those transmissions. The invention also provides algorithms designed to help parents learn how their baby moves from a relaxed/calm state to one that requires attention from the parents. The invention allows parents (or one or more caregivers) to simultaneously monitor multiple children at once from the basic level (e.g. determining if they need to be fed, or changed,) to a very detailed level (e.g., $O_2$ blood saturation levels, heart rate, among others). The modularity of the invention (e.g., the number of transmitters, controllers, wrist bands, sensors) provides the number of caregivers and number of children/patients to be user-determined. The creation of better reports from the sensors of this system aid parents in providing a high-frequency of measurements each day to provide pediatricians and/or other doctors a strong data set to monitor the baby's well-being over a long timescale. The assemblage of data from many children can help researchers understand and better constrain the conditions that lead to sudden infant death syndrome. The system simultaneously monitors the child and parents' sleep cycles. The invention analyzes the sleep cycle state of the caregivers to determine which caregiver shall be awoken based on where the caregiver is in their sleep cycle. A realization of this invention is that the caregiver who is in the lighter parts of their sleep cycle will be awoken. The invention analyzes the sleep cycle of the baby to wake the parents prior to the baby reaching a high-stress state. The caregivers will be able to choose between using the sleep cycle analysis versus choosing their own alert schedule. The system anticipates when a baby is about to require attention and thereby notifies parents of the need prior to the baby awakening. This feature leads to the parents tending to their baby prior to the baby reaching a heightened state of anxiety which allows for both the baby and the parents to return to their original activities or go back to their sleep cycle more quickly and easily. The invention provides a sound recognition software that determines what a baby requires when the baby makes different sounds and based on the vitals. The invention includes an algorithm and monitoring system that allows parents to link their sleep quality and quantity to aspects of their daily life (e.g., exercise regimen, alcohol consumption, etc.) to learn how to achieve better sleep quality and quantity. The invention provides a novel mechanism for a baby to continue feeling a mother's heartbeat after birth. This invention provides a mechanism to consistently capture and record a baby's first words. The invention includes random patterns of vibrations and/or sounds in which the randomness specifically bypasses a person's conditioned state to constant, expected, or periodic stimuli and hence more efficiently triggers the recognition of the need of the caregiver to respond to the patient/alert. By relying on vibration to alert the parents and determining the baby's needs through sound analysis, among others, the invention provides a global solution for caring for a child who has one or more hearing impaired caregivers.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1:
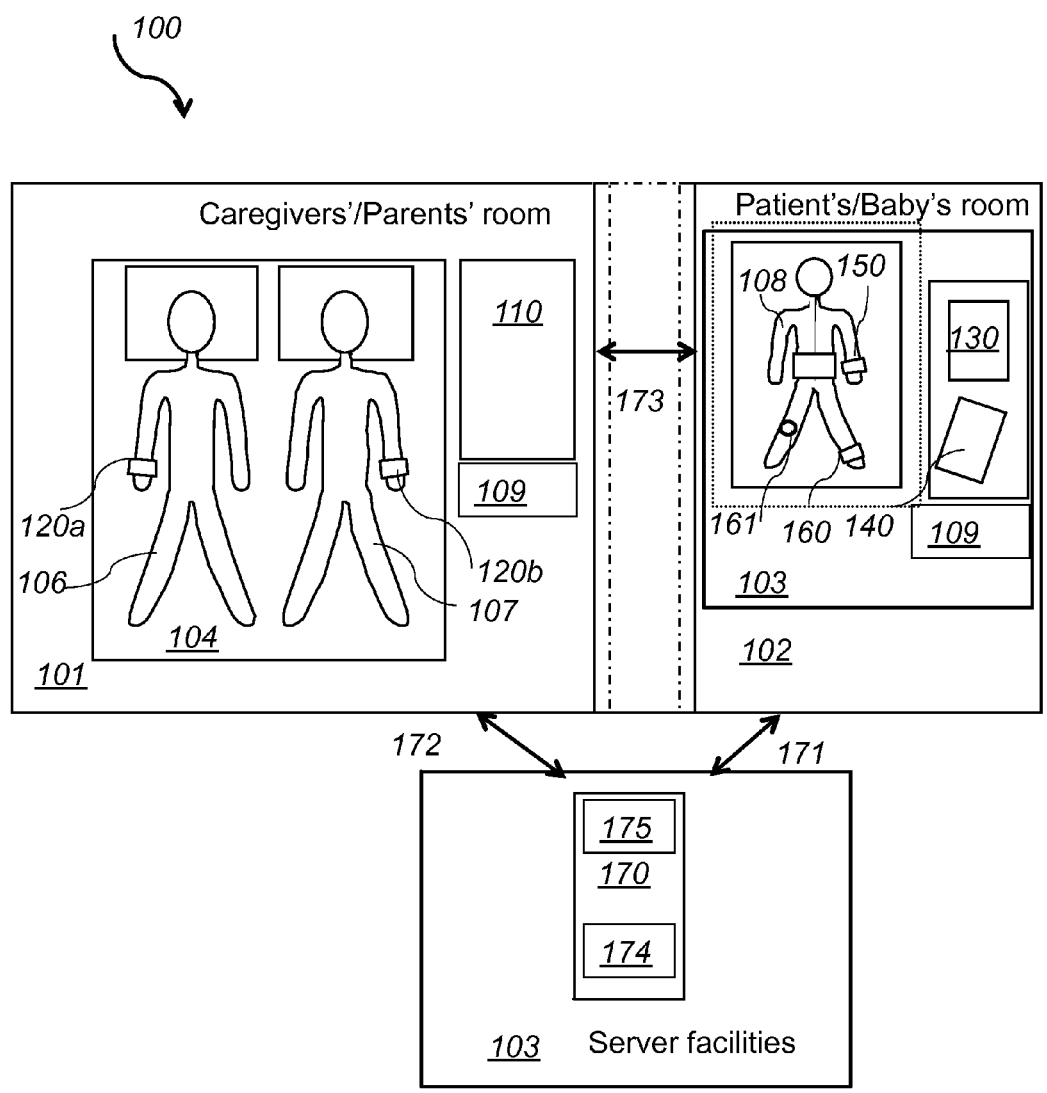
FIG. 1 is an overview diagram of the human monitoring system according to this invention.

Referring to FIG. 1, a human monitoring system 100 includes a transmitter 130, an external controller 110, two caregiver/parent wristbands 120a, 120b, a patient/baby sensor system 103, charging stations 109 for the system, and online secure servers 170. The patient/baby sensor system 103 includes a video camera 140, a baby wristband 150 and additional baby sensors 160, 161. The online secure servers are configured to communicate with the caregivers'/parents' room 101 components and the patient's/baby's room 102 components and to store and process the outputs of the sensor system 103 and to generate corresponding alerts that are then sent to the parents. The transmitter 130 is placed in the patient's/baby's room 102 and preferably in the vicinity of the person 108 to be monitored. The external controller 110 and the parents' wristbands 120a, 120b are placed in the caregivers'/parents' room 101 with the parents 106, 107 conducting the monitoring. In one example, the wristbands 120a, 120b are worn around the wrists of two parents 106, 107, respectively, and the controller 110 is placed in the room where the parents sleep. The patient/baby sensor system 103 is placed in the patient's/baby's room 102. In one example, the baby's wristband is worn around the wrist of the baby 108, and the video camera 140 is placed in the vicinity of the baby and the video camera lens is oriented so that the camera captures the image of the baby in the room. Additional sensors 160 are worn around the baby's ankles, thighs, waist or chest and are configured to monitor the baby's heartbeat, temperature, motion, and oxygen saturation level. Skin sensors 161 may also be placed on the baby's skin for sending vital organ information to the controller 110. The charging station 109 is placed near a power source. The servers 170 are located offsite from the parents' room and the baby's room and are connected to the monitoring system remotely via a wireless network, such as the Internet. Two-way communications 171, 172, 173 exist between all system components. Communications 171, 172, 173, may be wired or wireless communications and the wireless communications may be the Internet, 4G, 5G, via Wireless Local Area Networks (WLAN) (i.e., 802.11a, 802.11b), via Wireless Wide Area Networks (WWAN) or via Personal Area Networks (PAN) (i.e., Bluetooth, Infrared). The controller 110 is a wireless or wired device and may be a mobile phone, a personal digital assistant, a pager, a wireless laptop computer, a tablet, a smart watch, a personal computer, a television remote control, or combinations thereof.

Figure 2:
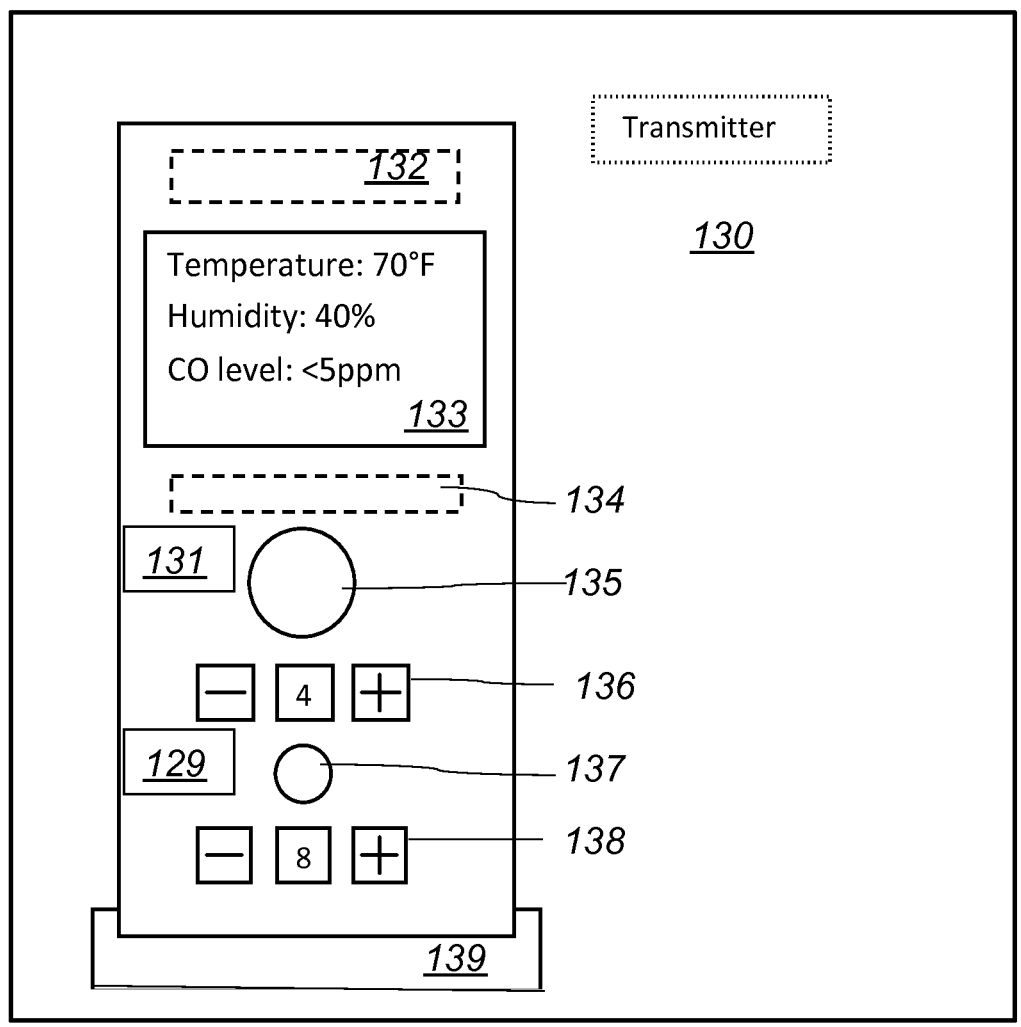
FIG. 2 depicts the transmitter used in the human monitoring system of FIG. 1.

Referring to FIG. 2, transmitter 130 includes a processor 131, a data recorder/storage, a telecommunications unit 132, a screen display 133, room sensors 134, a speaker 135, a speaker volume controller 136, a microphone 137, microphone threshold level controller 138, and a transmitter charging station 139. The microphone 137 picks up sound from the baby's room and the transmitter 130 is configured to transmit the sound signal to the controller 110 and the wristbands 120a, 120b in the parents' room and to the server 170. If the sound signal has amplitude stronger than a user-determined threshold, or after internal processing of the data determines that the child needs care, the transmitter 130 sends an alert to the controller 110 and/or the parent wristbands 120a, 120b. Room sensors 134 include a room temperature sensor, a CO detector, a $CO_2$, detector, a humidity sensor, an air quality sensor, and a smoke detector. To provide a quick response in case of emergencies, the transmitter 130 performs preliminary onboard analyses of the sensor data via the processor 131 and notifies the parents accordingly. For more computationally intense and/or non-emergency analyses, the transmitter 130 sends the sensor information to the external controller 110 and/or the online servers 170 for further analysis. In this case, the external controller 110 and/or the online servers 170 alert the parents 106, 107 and the parent-designated outside parties, e.g., other family members, caregivers, or neighbors, among others, if any of the sensors detect user-determined and/or predefined unsafe conditions. The transmitter 130 records and stores the sound data from the baby 108 in the local storage 129 and also sends the data to the external controller 110 and/or the online servers 170 for remote storage 112, 175, respectively. This feature enables the parents 106, 107 to access past events for pleasure and/or diagnostic purposes. In particular, it allows for capturing lifetime events such as the very first words of the baby 108. In addition, it provides a mechanism for parents to learn and understand how their baby moves from a relaxed/calm state to one that requires attention from the parents. The features of the transmitter 130 are controlled on the device via the speaker volume controller 136 and the microphone threshold level controller 138. The features of the transmitter 130 are also controlled remotely from both the external controller 110 and the wristbands 120a, 120b, which allow for greater ease in the user experience. A change in the transmitter settings from any of these locations is directly reflected at all other locations thanks to the two-way communications 171, 172, 173 between the system components. By adding multiple transmitters 130 and baby sensor systems 103, parents can monitor multiple children simultaneously from a broad level (e.g., if they need to be fed, changed, among others) to a very detailed level (e.g., $O_2$ saturation level, heart rate, among others). In such a case, a baby specific transmitter 130 notifies the parents as to which baby requires attention, and based on input from the system specific sensors 140, 150, 160, 161, a monitoring application or smart phone application (SPA) 600 running on the controller 110, and a cry analyzer 640, assess what that the baby needs, as will be described below.

Figure 5:
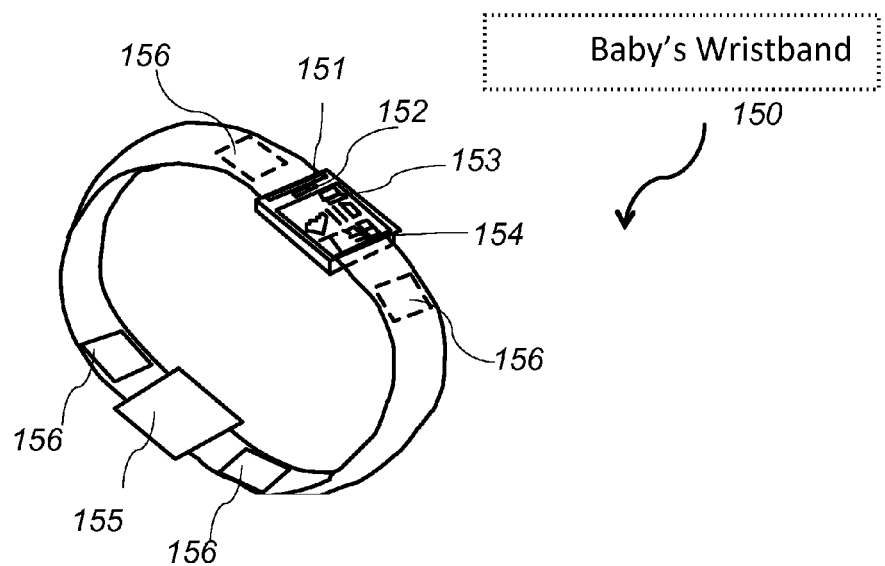
FIG. 5 depicts the baby's wristband device used in the human monitoring system of FIG. 1.

Referring to FIG. 1 and FIG. 5, the baby sensor system 103 includes a video camera 140 and sensors 150, 160, 161 that attach to the baby in the form of bands either for the wrist (150), or ankle, waist, abdomen, leg, or thorax (160) and other sensors that attach to the baby's skin (161). This sensor system 103 monitors the baby's heart rate, breathing rate, temperature, O₂ saturation, motion, and sleep cycle. The baby sensor system 103 transmits data from the video camera 140 and all of the above sensors 150, 160, 161 to the transmitter 130, the external controller 110 and/or to a secure server 170 via network connections 171, 172, 173. The transmitter 130 conducts preliminary on-board analyses of the data via processor 131 for quick intervention in case of emergency situations (e.g., the baby stops breathing). The external controller 110 and/or the online servers 170 conduct the more in-depth and computationally expensive analyses via processors 111, 174, respectively. The analyses are assembled into reports by the external controller 110 and/or the online servers 170, and the reports are configured to be viewed from the external controller 110, or any other computing device in the system, such as the wristbands 120a, 120b, servers 170, or any other networked computer. In addition, parents 106, 107 use the external controller 110 to email and/or print the reports, via a networked printer (not shown). The baby sensor system 103 sends alerts to the parents' wristbands 120a, 120b via the external controller 110 in cases where it detects irregularities in any of the sensor readings or the integrity of the system is compromised (i.e., weak or lost network connection or a defective component). Sensors 150, 160, 161, in combination with the cry analyzer 640 on the controller 110 and/or server 170 and the smart phone application 600, recognize, predict and anticipate when the baby is about to require attention and thus wake up parents in advance. This early notification allows the parents to respond to the baby when the baby is in an earlier state of awakening in order to prevent the baby from achieving an increased level of unhappiness or anxiety. Thus the system reduces the risk and intensity of the baby's crying and allows the baby to fall back asleep more easily which, in turn, allows the parents to return to sleep more quickly and easily. In addition, the sleep experience of the parents is also enhanced by the fact that waking up only the on-duty parent can be made more gradual and, hence, smoother as the need for a parental action is detected sooner.

As was mentioned above, the baby sensor system 103 includes a video camera 140 that is focused on the baby. The video camera's 140 ability to focus, move, and zoom is controlled by the external controller 110. The video feed is sent directly to the external controller 110 and/or to the secured server 170 via the network connections 173, 171, respectively, for the parents and/or other authorized people to view. Hence, the video feed can be viewed from the controller 110, or any other computing device, such as the wristbands 120a, 120b, in embodiments where the wristbands 120a, 120b include screens. This video feed is also saved on the storage device 112 of the external controller 110 and/or the storage device 175 of the online servers 170 for parents to view later or share via social media.

Referring to FIG. 5, the baby's wristband 150 is worn around the baby's wrist and monitors the baby's vital signals. Wristband 150 includes a speaker 151, a microphone 152, a battery level indicator 153, a screen 154 indicating the baby's conditions, a wristband adjuster 155 and vibrators 156. Wristband 150 allows the baby to listen to and/or feel the parent's heartbeat via the speaker 151 or the vibrator 156, respectively. Screen 154 displays the baby's vital parameters such as the body temperature, heartbeat, O₂-saturation level, among others. Parents determine which sensor information they want to display on the wristband screen 154. The baby's wristband 150 also has the capability to send alerts to the caregivers and/or outside parties via the network connections 171, 173, if unsafe conditions are detected. As an example, out of range body temperature, heartrate, and/or breathing sequence would cause the wristband 150 to start an alert sequence by itself. This capability aims to prevent tragic accidents, such as overheating of children that are left or forgotten in cars.

Figure 4:
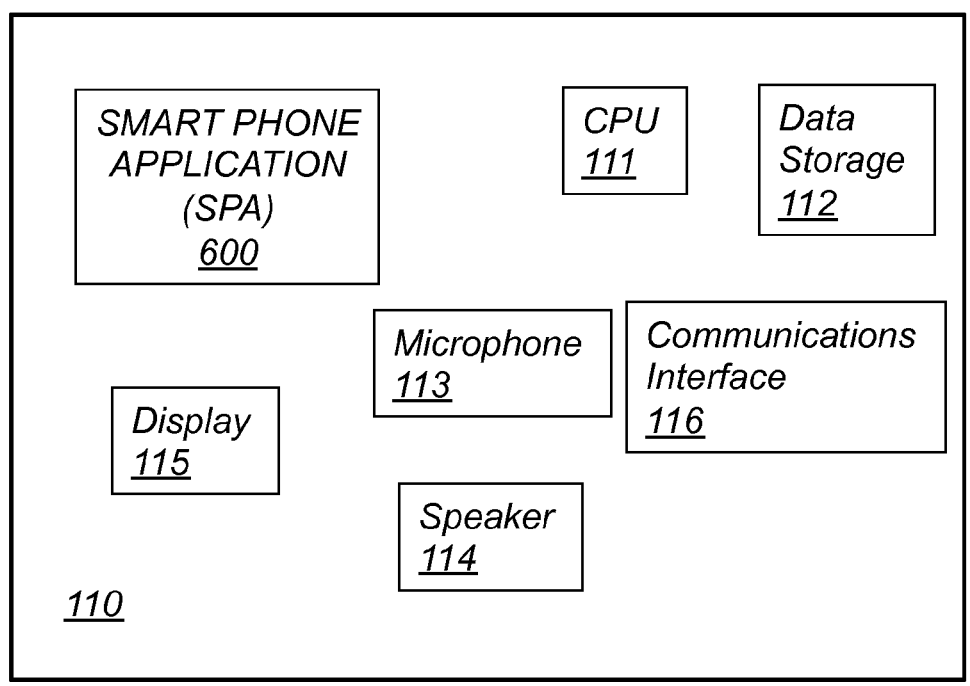
FIG. 4 depicts the controller used in the human monitoring system of FIG. 1.

Referring to FIG. 4, the external controller 110 includes a processor 111, data storage 112, microphone 113, speaker 114, controls for the microphone and speaker (not shown), a display 115, a communications interface 116 and smart phone application (SPA) 600. The external controller 110 acts as both the controller for the entire system 100 as well as a relay station for signal transfer between the transmitter 130, the parent wristband devices 120a, 120b, and the baby sensor system 103. The transmitter 130, the parent wristband devices 120a, 120b, and the baby sensor system 103 also communicate with each other independently of the external controller 110. Parents control the entire system 100 through the software application 600 (Smart Phone Application or "SPA"), that is installed and runs on the external controller 110. The external controller 110 is a smart mobile phone or other device of similar capability. The external controller 110 provides centralized control of the system 100 as well as the ability to share the signals with other people and devices. The signal sharing includes, but is not limited to, audio and video signals. The external controller 110 also allows the parents to designate who is "on-duty" and "off-duty" and to set up and modify the on-duty/off-duty schedule, as will be described below. As was mentioned above, multiple channels of communication are used to increase the signal robustness and security, but also to optimize the energy consumption. The communication channels include Bluetooth or Internet (Wi-Fi or 4G) for transmitting sound signals and video transfer and radio for system alerts. The application SPA 600 includes sound recognition software, which distinguishes what a baby needs, based on the sounds from the baby, the inputs of additional sensors, and user input from parents, as will be described below.

Figure 3A:
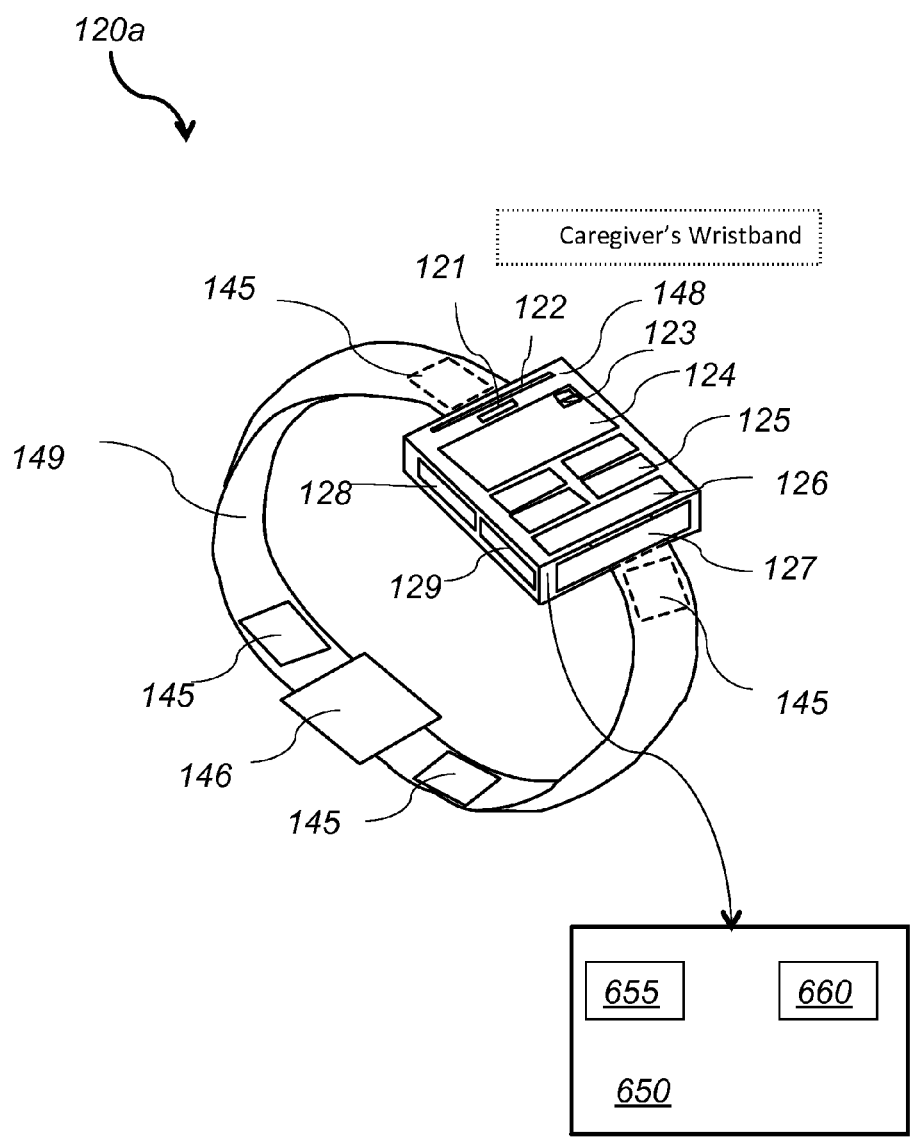
FIG. 3A depicts the caregiver's wristband device used in the human monitoring system of FIG. 1.

Referring to FIG. 1 and FIG. 3A, the monitoring wristband system 104 includes at least two wristband devices 120a, 120b that are worn by parents 106, 107, respectively. Each wristband device 120a includes a monitoring device 148 removably attached to an adjustable band 149. Monitoring device 148 includes vibrator pads 145, a speaker 121, a speaker activation button 129, a microphone 122, an LED display touch-screen 124, and a battery level indicator 123. Speaker 121 can be programmed to be activated by pressing the speaker activation button 129 for nighttime, or to be an out-loud speaker for daytime use. Alternatively, two separate speakers may be used, one button activated for nighttime use and an out-loud speaker for daytime use. Vibrator pads 145 are arranged on multiple locations along the band 149. The parents 106, 107 use the application SPA 600 to select when they want the vibrator pads 145 and/or the speaker 121 to be activated. Those notification mechanisms alert the parents 106, 107 when the baby 108 requires attention. They also notify parents 106, 107 of incoming phone calls, text messages, emails, and other application alerts, such as Facebook, Whatsapp, phone calls, text messages, e-mails, Skype calls, among others. For alerts concerning the baby 108, the LED touch-screen 124 notifies the parents 106, 107 in advance of what the baby needs so they are prepared when they get to the baby. For the other application alerts the LED touch-screen 124 tells parents who is contacting them and allows them to answer the calls using the embedded speaker/microphone system or answer the text messages, and emails, among others. In addition, the LED touchscreen 124 provides other information, such as time, battery level 123 ambient temperature, and location among others. While the application SPA 600 acts as the main controlling application of the system 100, the wristband device 120*a* also provides control over aspects of the system, such as the sound threshold at which the parents want to be contacted, and allows the parents to input and change the system parameters via the wristband device 120*a*. The system parameters that were entered and changed via the wristband device 120*a* are then updated within the SPA 600 and are recorded on all other parts of the system. The wristband LED screen 124 provides the ability for parents to monitor the information from the baby sensor system 103. The LED screen 124 also broadcasts the video feed from the video camera 140.

The parent's wristband device 120*a* further includes a processor 650 that runs a sleep cycle monitoring and analyzing application 655. The sleep cycle monitoring and analyzing application 655 documents how long the parents have slept in total and how long parents have stayed in different states of sleep (i.e., deep sleep or lighter sleep) and can be used to trigger the alert sequence. Through the wristband devices 120*a*, 120*b* and/or the SPA 600, the parents input aspects about their daily activities such as, exercise regiment, alcohol consumption, stress level, nutrition, among others and those inputs are correlated with the sleep cycle quality and quantity they receive at night. Over the course of time, the parents use the system to analyze their own sleep quality and quantity and how that relates to the factors occurring in their everyday life, such as stress, food/alcohol consumption, exercise, among others. The parent's wristband device 120*a* further includes a fitness analyzing application 660. In combination with the SPA 600, the fitness analyzing application 660 detects the fitness activities of the wearer and conducts diagnostic tests to determine activity level, calories burned, and heart rate over time, among others. The data from these tests are assembled into reports within the SPA 600 or via the online server 170 and can be viewed on the SPA 600 or the wristband device 120*a* via the LED screen 124, or can be printed via a wireless or wired networked printer, or emailed to the parents.

The wristband device 120*a*, further includes wristband adjusters 146 that allow the band 149 of the device to be adjusted for comfortable wear by the users. The position and the setting of the vibrators 145 on the band 149 are specifically chosen to optimally alert the user via vibration. The frequency range chosen is within the range of 2-1000 Hz. Preferably, the vibration frequency is lower than 300 Hz, as this frequency range is below the audible range of the human ear. This is also the frequency range that resonates with human tissues/bones and hence requires a lower amplitude signal in order to be sensed. Therefore the risk to be sensed or heard by the off-duty parent is mitigated. In addition, the system utilizes specific wave fronts for the vibrations. In one example, the system utilizes wave fronts composed of random step-functions since the response of a human brain decreases for predictable stimuli.

This monitoring wristband system 104 monitors the parents' and the baby's heart rates for their visual, audio, and vibratory reproductions. Upon selection via a button 128, the parents' wristband device 120*a* plays via a speaker 121 or vibrates following the baby's heartbeat so that parents can monitor the baby, and specifically feel the different levels of the baby's emotions. The baby's wristband device 150 allows the baby to listen to sound and/or feel vibrations originating from the parent's heartbeat. This functionality provides continuity between the pre-birth and post-birth acoustic environments, and hence the continuation of the baby receiving a parent's heartbeat should comfort the baby.

Figure 3B:
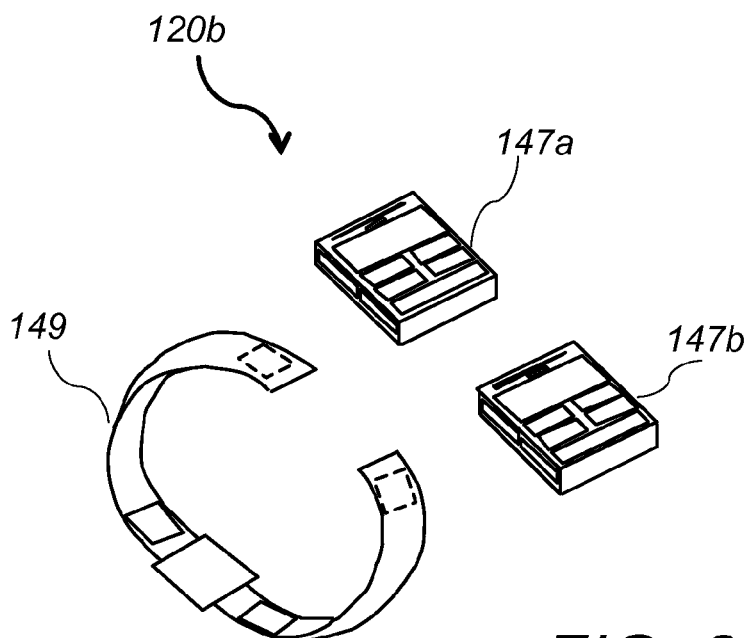
FIG. 3B depicts the daytime and nighttime removable wristband device components used in the human monitoring system of FIG. 1.

Referring to FIG. 3B, the wristband device 120*b* includes nighttime 147*a* and daytime configurations 147*b* that are removably attached to band 149. The nighttime configuration 147*a* is optimized for use during the night while the daytime configuration 147*b* is optimized for daytime care. The daytime configuration 147*b* includes an out-loud speaker 121 that is specifically designed to broadcast sound out-loud, while the configuration for the night time configuration 147*a* includes a vibrator 145 and a speaker 121 designed to work at lower sound level and with a design configured to focus the sound in the vicinity of the wrist so the parent can hold the speaker to his/her ear and thus not disturb his/her partner. In one example, speaker 121 has a parabolic shape. In this embodiment 120*b*, the batteries 127 are embedded inside each configuration 147*a*, 147*b*. Each configuration 147*a*, 147*b* is charged when not in use. The embedment of the batteries 127 significantly reduces system bulkiness.

The operation of the nighttime configuration 149*a*, including the robust system of alerts, was described above. The operation of the daytime configuration 149*b* includes the following. During the day, the out-loud speaker 121 on the wristband device 120*b* is activated such that the wristband device 120*b* acts as a hands-free baby monitor thereby allowing parents to freely accomplish their tasks throughout the day without having the inconvenience of caring around a standard baby monitor. Using the SPA 600, the parents have full control over determining when the system switches between daytime and nighttime modes. The wristband devices 120*a*, 120*b* are water resistant so that they are robust against daily activities. In addition, both during daytime and nighttime, the system self-monitors its ability to work adequately. For example, if the battery level 123 or the signal quality/strength is too low, or the signal is lost or about to be lost, then the wristband-wearer is alerted.

Parents 106, 107 use the microphone 122 on the wristband device 120*a* to broadcast a voice signal via the speaker 135 in the transmitter 130 into the baby's room 102. Parents 106, 107 can also record messages by using the microphone 122 on the wristband device 120*a* or by using the SPA 600 and arrange to have those messages be played at pre-scheduled times via the SPA 600 or on-command using the wristband device 120*a* or the SPA 600. As with other components of the system 100, the settings of the wristband device 120*a* are programmable remotely by the SPA 600. The settings of the wristband device 120*a* are also controlled on the wristband device. Setting changes in either system component are updated in the other components so that each part of the system is synchronized.

The parent wristband devices 120*a*, 120*b* are powered via the battery 127. Battery 127 may be a removable battery that can be removed and plugged directly into a battery charger. In other embodiments, battery 127 is embedded in the device and the entire device is removed from the band 149 and charged when not being in use, as was described above in the case of the nighttime and daytime configurations 147*a*, 147*b*. In yet other embodiments, battery charging occurs by connecting a power source to ports, such as mini-USB, or audio-jack, among others. The included battery charging system allows for 24/7 usage of the device.

The data from the baby monitoring sensors 140, 150, 160, 161 are collected by the transmitter 130 and then sent via a protected network connection 171 to the online servers 170. The online servers 170 store the data in storage 175 and process the data via the processor 174. Storage of the baby monitoring data provides a record for the parents that is beneficial at the personal level (e.g., tracking their baby's behavior/mood, keeping track of the baby's first words,) and at the medical level (e.g., having records of the baby's heartbeat, activity level, and vital signals that they can share with a doctor). The processing capabilities of processor 174 enable more detailed, on-the-spot analyses of the sensor outputs for a better monitoring of the baby. If the analyses suggest that the baby may require attention, an alert is sent by the online servers 170 to the SPA 600 via connection 172, which forwards the alert immediately to the on-duty parent's wristband 120a. In addition, two reports are sent by the server 170 to the SPA 600, including a summary report and a detailed report. Upon arrival at the SPA 600, the reports are directly forwarded to the parents' wristband devices 120a, 120b. These reports are also available for email and/or printing.

Referring to FIG. 6, FIG. 6A-FIG. 6D, the monitoring application or smart phone application (SPA) 600 includes an alert sequence menu 610, a scheduler 620, a report menu 630 and a cry analyzer 640. SPA 600 runs on the controller 110 and controls the functions of the transmitter 130. Parents 106, 107 use the SPA 600 to set the minimum threshold of noise required for them to be notified via their wristbands devices 120a, 120b. One reason for setting this threshold is to prevent the system from sending false positive notifications due to outdoor noises such as cars driving by, sirens, or outdoor equipment, among others. The lowest threshold alerts parents of any noise detected by the microphone 137 on the transmitter 130. The SPA 600 also receives vocal information from the parents through the microphone 113 on the external controller 110 or the microphone 122 on the wristband devices 120a, 120b and transmits the vocal information to the baby through the speaker 135 on the transmitter 130. In this manner, parents can talk to the baby remotely, or play sounds, such as lullabies or sounds that mimic the internal acoustical environment of a mother's belly, among others. This feature is especially beneficial if the baby simply needs to hear the parent's voice to calm down. As was mentioned above, the parents 106, 107 use the SPA 600 to record messages that they can play to the baby 108 through the speaker 135 on the transmitter 130 by indicating on the SPA 600 or via their wristband devices 120a, 120b when they want those messages to be played. The parents can set times for the messages to be played or send them instantaneously using the SPA 600 or the wristband devices 120a, 120b.

The SPA 600 works in combination with the transmitter 130 to train and refine the cry analyzer 640 of the system. Each time the baby cries, the transmitter 130 sends the cry information to the SPA 600. After the parents tend to their baby, they select from the SPA 600 what their baby required 641, i.e., to be fed, to be changed, to be burped, to be comforted, among others, as shown in FIG. 6D. The SPA 600 then uses a dedicated learning algorithm to predict what future cries from the baby are indicating. During future cries, when the parents are notified that the baby requires attention, they are also notified about the likely causes for the notification 641 (e.g., if their baby needs changing, feeding, etc.) as well as the probability of these possible causes 642, shown in FIG. 6D.

The transmitter 130 and the SPA 600 work in combination to form the notification analyzer. This notification analyzer uses the information provided by the cry analyzer 640 in combination with the sounds and sensor information from the transmitter 130 and baby sensor system 103, respectively, to determine the conditions that existed for the baby prior to the baby making audible noise (i.e., the process in which the baby becomes upset via the realization that he/she requires attention but has not yet obtained it). An example of such a situation would be at night when the baby starts to wake up and would typically require a feeding/changing. The notification analyzer recognizes when this situation occurs (i.e., as the baby is waking) and notifies the parents prior to the baby fully waking/becoming upset. The parents can then tend to the baby prior to the baby reaching a heightened state of anxiety. With the baby's needs filled prior to becoming upset, the baby falls back asleep much more easily thus requiring less time from the parents and leading to less anxiety for the parents directly translating into a quicker and easier return to their own sleep cycles.

The baby sensor system 103 sends the information it collects about the baby to the transmitter 130, which completes preliminary on-board investigation of the data and also relays the data to the external controller 110 and/or online servers 170 for further analysis. The on-board investigation on the transmitter 130 is targeted towards quick detection of problems (e.g., drops in the baby's $O_2$ saturation level, detection of smoke, etc.). In addition, the external controller 110 continuously monitors the sensor information in order to make sure that the baby is in safe conditions (e.g., to act as a prevention to Sudden Infant Death Syndrome (SIDS)). The external controller 110 and/or the server 170 store the sensor system information in storages 112 and 175, respectively, and the SPA 600 and the server 170 create reports concerning the data from each sensor and make the raw data and/or the reports available to the parents via the SPA report menu 630, shown in FIG. 6C. The SPA 600 also provides the ability to email the reports to the parents and/or to print the reports via a networked printer. Information relative to specific sensors is directly accessible on the parent's wristband devices, e.g., the baby's temperature, heartbeat, $O_2$ saturation, among others. The baby's wristband 150 also has the capability to send alerts to the caregivers and/or outside parties via the communication networks 173, 171, if unsafe conditions are detected. As an example, unsafe temperature, heartrate, and/or breathing sequence would cause the wristband device 150 to start an alert sequence by itself.

As was mentioned above, parents 106, 107, use the SPA 600 to stream video and sound from the transmitter 130 to their watchband devices 120a, 120b. This allows the parents to monitor the movement of a child, receive alerts and intervene in cases when the child tries to climb out of a crib. The SPA 600 also provides for the video and sound data to be stored so that the parents can see what happened with the baby prior to being notified by the SPA or prior to them accessing the video portion of the SPA out of their own interest. This feature proves beneficial in the parents learning how their baby moves from being happy to upset. The video feature includes at least two videos playing simultaneously where one shows the real time streaming while the other shows the recorded video from the time window of the parent's choosing. In this manner, the parents can see the current state of the baby as well as the past state. The SPA 600 provides the control system for parents to select how the two videos play (e.g., what sounds are broadcasted during playback, and what portions of video are played back). The SPA 600 allows uploading these saved videos with sound to the parent's social media platform of their choice (e.g., Facebook, Google+, YouTube, among others). The SPA 600 also provides easy transfer of the videos with sound to computers for permanent storage in order to provide parents a mechanism to save their memories.

Figure 6:
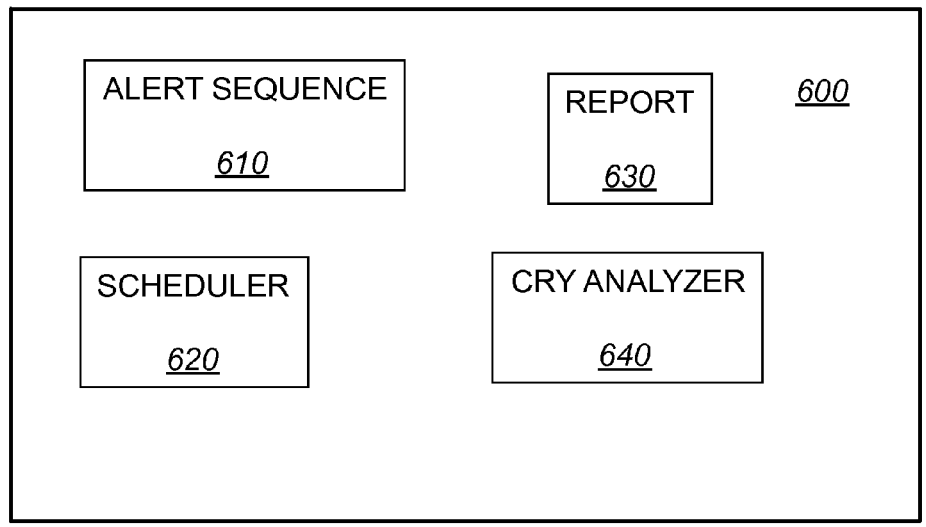
FIG. 6 depicts a block diagram of the smart-phone application (SPA) used in the human monitoring system of FIG. 1
Figure 6A:
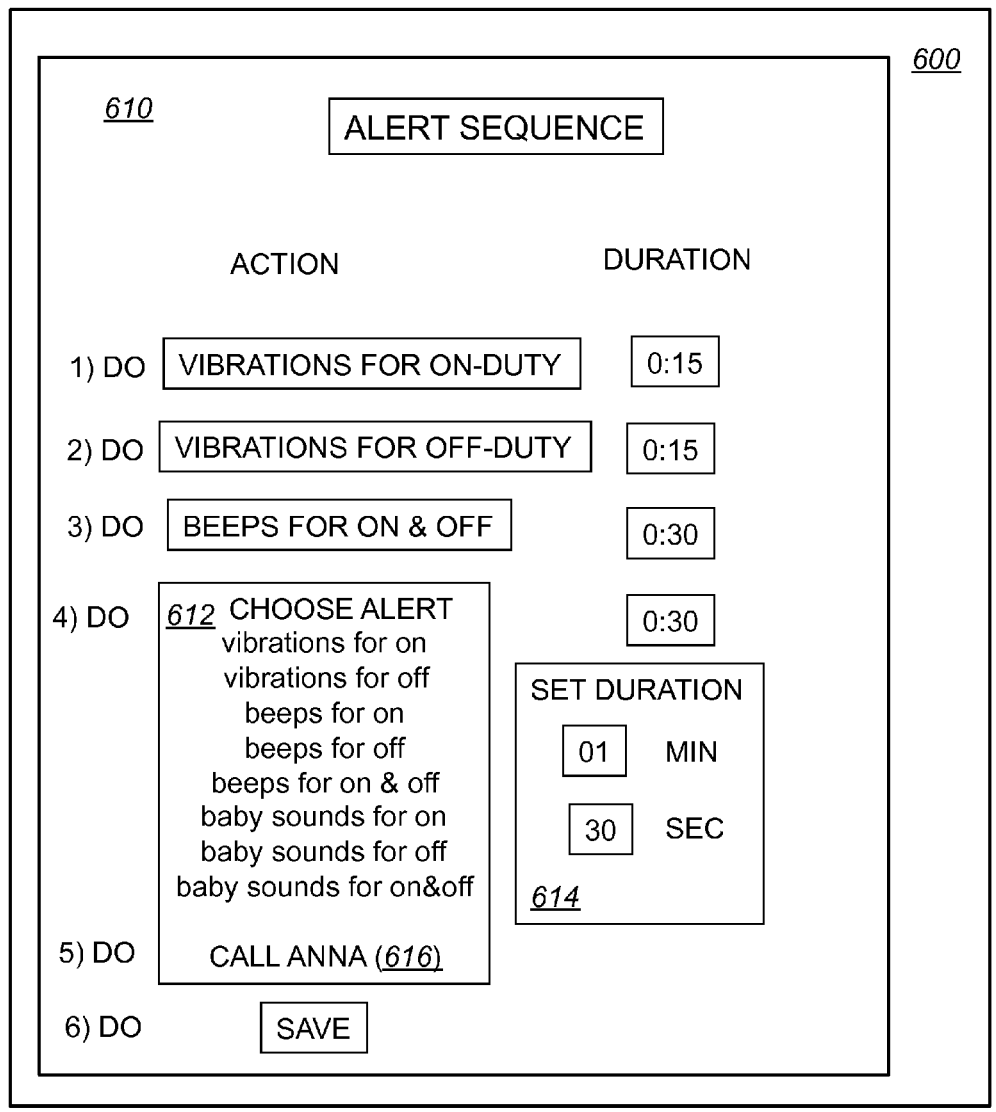
FIG. 6A depicts a user interface menu for setting an alert sequence in the SPA of FIG. 6.
Figure 6B:
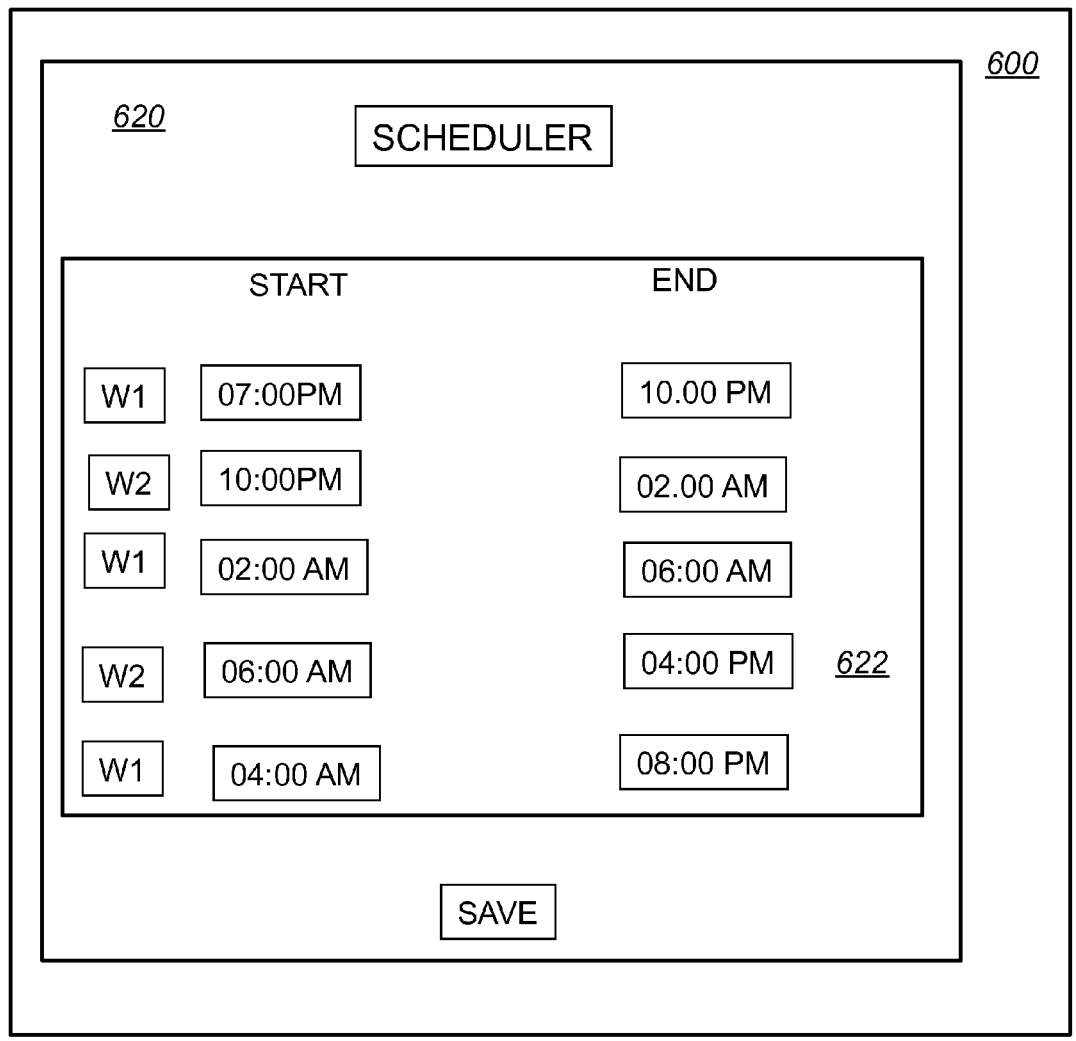
FIG. 6B depicts a user interface menu for setting the on/off-duty schedule in the SPA of FIG. 6.
Figure 6C:
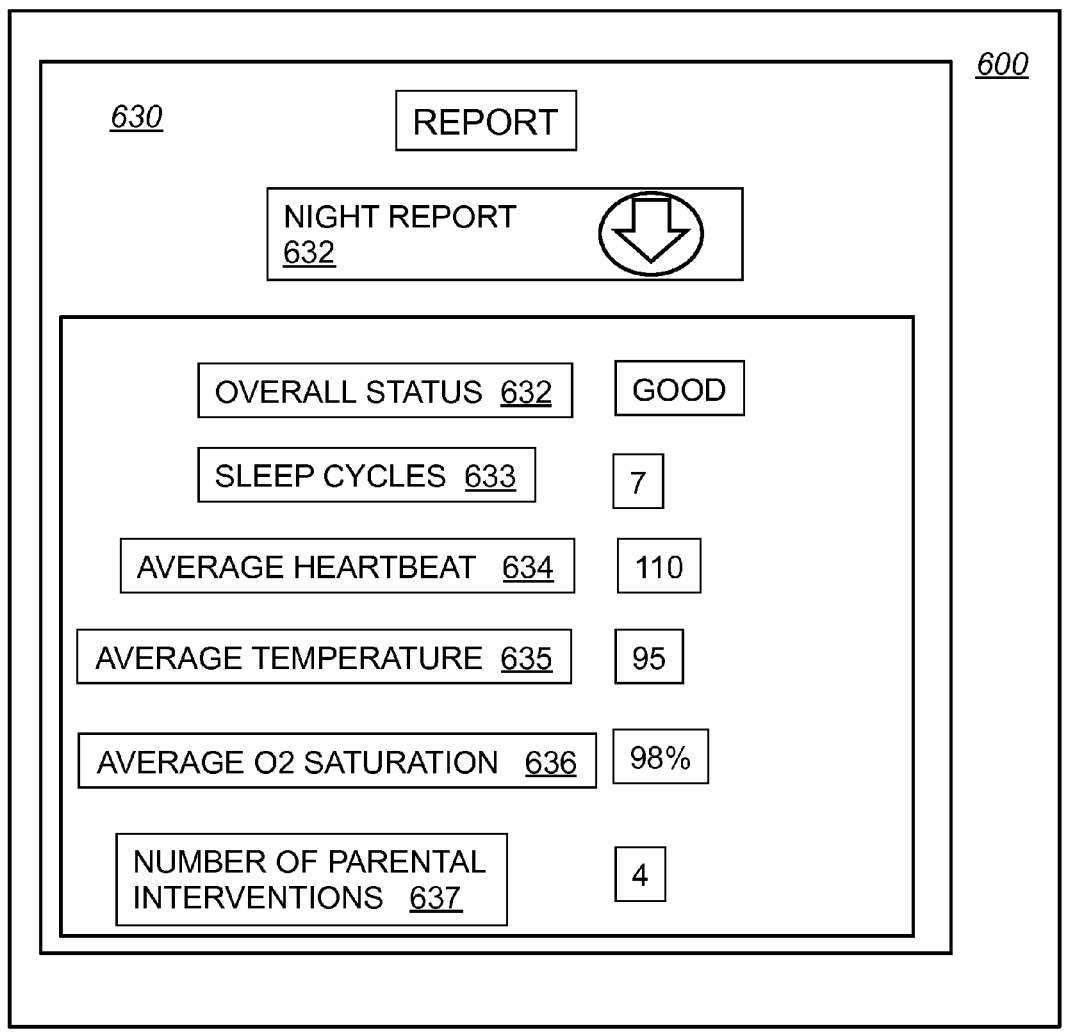
FIG. 6C depicts a user interface menu for generating a data analysis report in the SPA of FIG. 6.
Figure 6D:
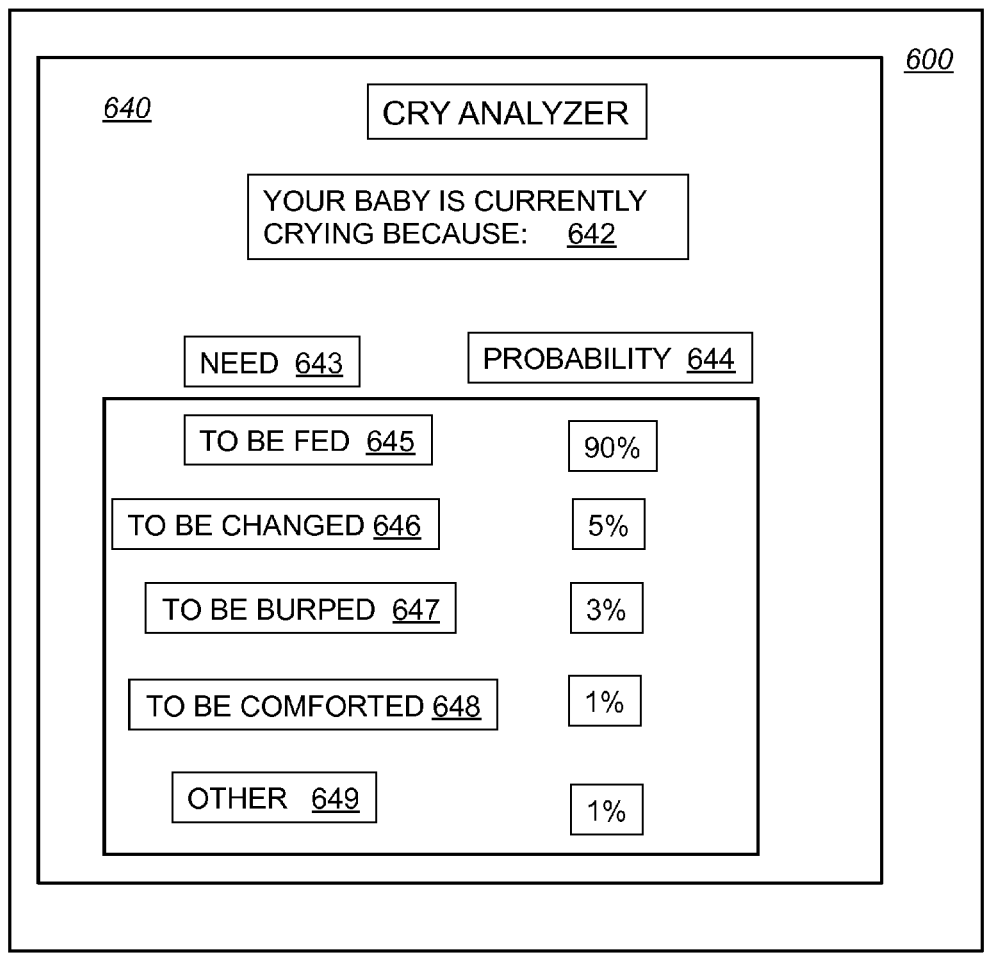
FIG. 6D depicts a user interface menu for a cry analyzer in the SPA of FIG. 6.

Within the SPA 600, the parents set how and when they would like to be contacted when the baby requires attention, via the alert sequence menu 610, shown in FIG. 6A. This includes the sound threshold that they require before they are contacted via the wristband devices 120a, 120b. This also includes a robust system of alerts for the wristband devices 120a, 120b, including vibrations, beeping, and baby sounds, among others. Using the scheduler 620 of the SPA 600, the parents designate when each wristband device 120a, 120b is on-duty and off-duty, as shown in FIG. 6B. Both wristband devices 120a, 120b can be placed as on-duty. When the SPA 600 determines that the parents need to be notified, it first sends the signal to the on-duty parent, as was set by the alert sequence shown in FIG. 6A. This alert first causes a vibration on the wristband device 120a. The notified parent then presses a button 129 on the wristband device 120a to activate a speaker 121 to hear directly from the baby so that they can hear if the baby requires attention or is simply cooing. The cry analyzer 640 will also provide them with an estimate of the most likely need of the baby at that time. The parent must then press the "alert received and treated" button 126 on the wristband device 120a to indicate that they have received the signal from the SPA 600. If they do not press button 126 within a parent-determined time window, then the off-duty parent's wristband device 120b vibrates and the off-duty parent has the same abilities as the on-duty parent to respond to the alert. The parent-determined time window for response was previously set (614) within the alert sequence menu 610 of the SPA 600. If the off-duty parent does not respond, then the speakers 121 on both wristband devices 120a, 120b become activated and transmit the sounds from the baby. The sound from the baby may also be transmitted to speakers 114 on the controller 110, if was so selected via the SPA. If both parents 106, 107 fail to indicate that they are responding to the baby at this stage, then both wristband devices speakers 121, and the controller device speaker 114 broadcast a loud alarm sound. If the parents still fail to respond, then the SPA 600 notifies parent-designated people outside of the parent's home. This robustness would notify outside parties in cases of dangers, such as fire, CO poisoning, break-ins, or any other situation where the parents fail to respond. The parents determine which outside parties are to be contacted (616) and how they are to be contacted via the alert menu 610, shown in FIG. 6A. Outside parties may be contacted via a phone call, text, or email, among others. If the parents fail to respond and the baby sensor monitors pick up smoke, unsafe CO levels, or any other unsafe conditions, then the SPA 600 can also notify the police/fire departments.

Additionally, at any point, the SPA 600 can be used to notify the parents through alternative methods such as text, email, phone calls to landlines and/or cell phones, among others. The sequence of alerts is fully customizable. Parents have full control over activating or deactivating the feature of contacting an external caregiver and/or the police/fire departments.

As the system 100 is built around two-way communications, the transmitter 130 can send alerts directly to the wristband devices 120a, 120b. The wristband devices 120a, 120b can send setting updates to the transmitter 130, such as updates concerning the threshold alert level or the on/off-duty schedule. We note that if a wristband device 120a, 120b does not have direct access to the transmitter 130, then it uses the SPA 600 as a relay station. If the SPA 600 cannot communicate directly with the transmitter 130, then the transmitter 130 passes the information through the online server 170 to the SPA 600 which then acts as a relay station to the wristband devices 120a, 120b. Also, if the transmitter 130 does not have a direct access to Internet via Wi-Fi, it uses the SPA 600 as a relay station using a mobile communication network connection to access the online servers 170. If the analyses on the online servers 170 suggest that the baby requires attention, then an alert is sent by the servers 170 to the SPA 600 via the network connection 172. The SPA 600 then forwards the alert immediately to the on-duty parent's wristband device 120a, 120b. In situations where the SPA 600 is outside the connection range of the system, (e.g., when a parent is at work or otherwise away from the baby), the parents can login remotely onto the online server 170 to view the information from the system, such as the video, audio, and sensor information data.

Figure 7:
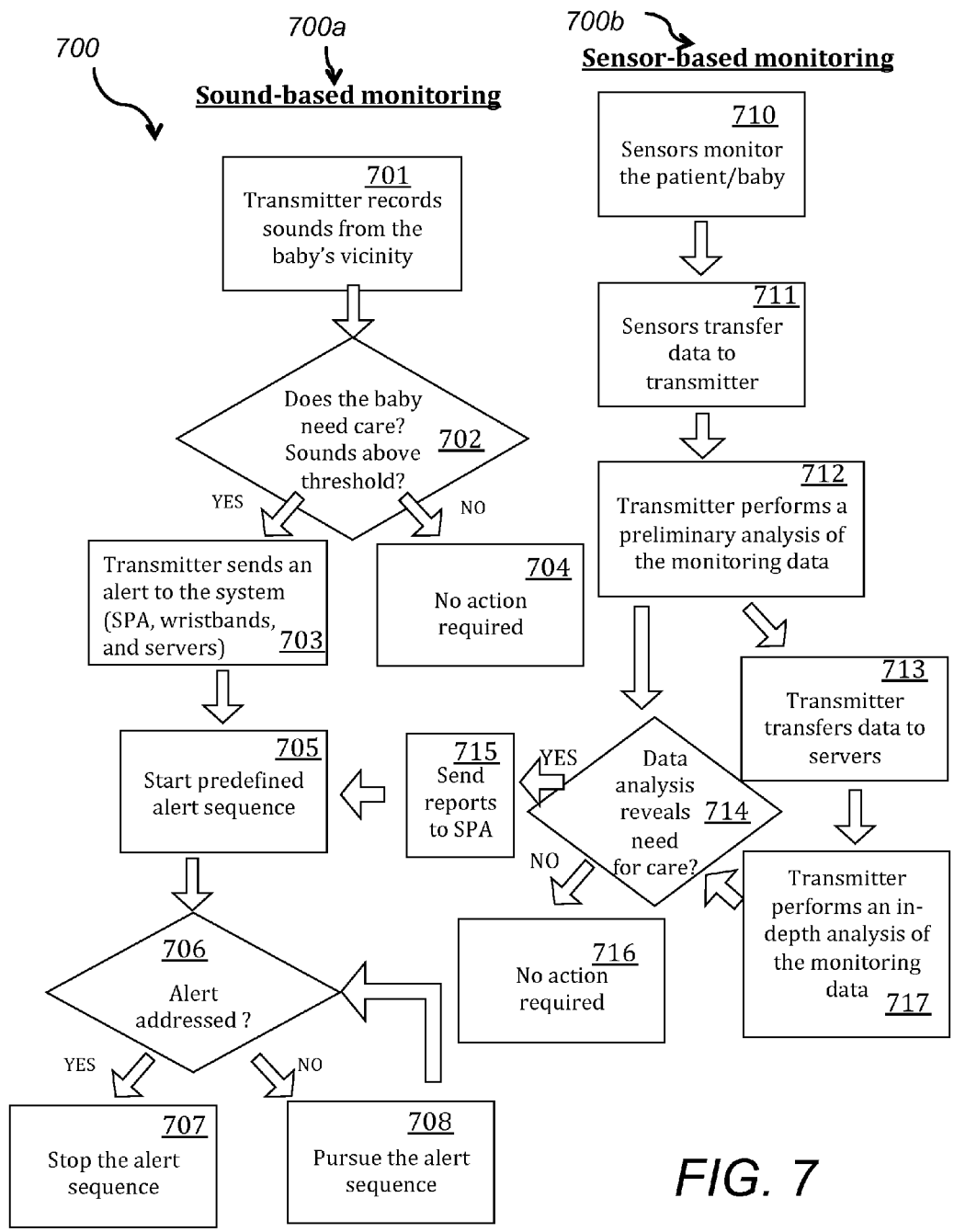
FIG. 7 is an overview diagram of the human monitoring process according to this invention.

In operation, the system 100 provides, two process paths 700a, 700b, for notifying the parents that the baby requires attention, as shown in FIG. 7. Path 700a provides sound-based monitoring and path 700b provides sensor-based monitoring. Referring to FIG. 7, in the sound-based monitoring process 700a, the following steps are included. First, the transmitter 130 receives sounds from the baby's vicinity (701), and then the transmitter 130 determines if the sound is above the set sound threshold and the baby needs care (702). If it is not, then no action is required (704). If the sound is above the set threshold and the baby is crying and needs care, then the transmitter 130 sends an alert to the system components including the SPA 600, parent wristbands 120a, 120b, and servers 170 (703). The predefined alert sequence is then started (705). An example of the predefined alert system is shown in FIG. 6A. Upon starting the alert sequence 610, the parent must now respond to the system (706). If the parent responds, then the alert sequence is halted (707). If the parent does not respond (708), then the alert system progresses through the defined steps, as shown in the example of FIG. 6A.

Referring to FIG. 7, in the sensor-based monitoring process 700b, the following steps are included. The baby sensor system 103 continuously monitors the baby and the conditions surrounding the baby (710). The sensor system 103 transmits the monitoring data on-the-fly to the transmitter 130 (711). The transmitter 130 performs a preliminary analysis of the monitoring data (712). The transmitter 130 simultaneously sends the monitoring data to the servers 170 for more detailed analyses (713). The transmitter 130 and the online servers 170 determine whether the baby needs care (712), (717). If both of them determine that the baby does not require care (714), no further action is taken (716). If either the transmitter 130 and/or the online servers 170 determine that the baby requires care (714), then they send reports to the SPA 600 (715). The SPA 600 then begins the predefined alert sequence (705), as was previously described. An example of the predefined alert system is shown in FIG. 6A. Upon starting the alert sequence 610, the parent must now respond to the system (706). If the parent responds, then the alert sequence is halted (707). If the parent does not respond (708), then the alert system progresses through the defined steps, as shown in the example of FIG. 6A.

Other embodiments include one or more of the following. The invention is applicable to any situation where caregivers attend people than need to be watched and cared for. In particular, the caregivers may be daycare employees, teachers, doctors, nurses, or other hospital or nursing home or assisted living facility employees, or prison employees. The people that need to be watched and cared for may be children, patients, residents of a nursing home or an assisted living facility, or prisoners.

Several embodiments of the present invention have been described. Nevertheless, it will be understood that various modifications may be made without departing from the spirit and scope of the invention. Accordingly, other embodiments are within the scope of the following claims.

What is claimed is:

1. A system for monitoring a user comprising:
   a transmitter positioned in a first location in a vicinity of the user;
   a sensor system to be worn by the user, configured to collect data comprising sound and image data of the user, a user's vital data and ambient condition data and transmit the collected data wirelessly to the transmitter;
   first and second monitoring devices configured to communicate wirelessly with the transmitter and to be worn by first and second caregivers of the user, respectively, wherein the first and second caregivers are located in a second location that is different from the first location;
   a controller located in the second location and configured to communicate wirelessly with the first and second monitoring devices and the transmitter;
   wherein the transmitter is configured to transmit wirelessly live data feeds to the first and second monitoring devices and to the controller and wherein the live data feeds comprise the sound and image data of the user and the user's vital data;
   an application comprising an analyzer configured to analyze the live data feeds and determine whether any of the collected data has a value above a predetermined threshold or out of a predetermined range and to send an alarm notification to at least one of the first and second monitoring devices in cases when at least one of the collected data has a value above the predetermined threshold or out of the predetermined range.

2. The system of claim 1, further comprising outside servers configured to receive wirelessly the live data feeds from the transmitter and to transmit wirelessly the live data feeds to the controller and the first and second monitoring devices.

3. The system of claim 1, wherein the application further comprises a scheduler configured to schedule times when the first and second caregivers are on-duty and off-duty for receiving and responding to the alarm notifications.

4. The system of claim 1, wherein the application further comprises a cry analyzer configured to analyze the sound data of the user and to determine whether the user is crying and to provide possible causes for the user's crying and to assign probabilities for such possible causes.

5. The system of claim 1, wherein the analyzer is further configured to analyze the live data feeds and determine whether the user is about to require attention and to send a notification to at least one of the caregivers prior to the user waking up or crying.

6. The system of claim 5, wherein the application is further configured to receive first and second caregiver's vital data, sleep pattern data and activity data and the analyzer is further configured to analyze the first and second caregiver's vital data, sleep pattern data, and activity data.

7. The system of claim 6, wherein the application is further configured to determine which caregiver is to receive the notification based on the analysis results of the first and second caregiver's vital data, sleep pattern data, and activity data.

8. The system of claim 1, wherein the application further comprises a report generator configured to report and display the collected sound and image data of the user and the user's vital data versus time.

9. The system of claim 1, wherein each of the first and second monitoring devices comprises a vibrator for providing a vibrating alarm notification to at least one of the first and second caregivers indicating that at least one of the collected data has a value above a predetermined threshold or out of a predetermined range.

10. The system of claim 1, wherein each of the first and second monitoring devices comprises a vibrator and a speaker for providing a vibrating alarm and a sound alarm notification, respectively, to at least one of the first and second caregivers indicating that one of the collected data has a value above a predetermined threshold or out of a predetermined range and wherein the vibrating alarm and the sound alarm comprise random patterns of vibrations and random patterns of sounds, respectively, and wherein the random patterns of vibrations and random patterns of sounds are configured to bypass the caregiver's conditioned and expected patterns of vibrations and sounds, respectively.

11. The system of claim 1, wherein each of the first and second monitoring devices further comprises a speaker for providing a sound alarm notification to at least one of the first and second caregivers indicating that one of the collected data has a value above a predetermined threshold or out of a predetermined range.

12. The system of claim 1, wherein each of the first and second monitoring devices further comprises a microphone for capturing a voice signal of at least one of the caregivers and transmitting the voice signal to the user wirelessly via the transmitter.

13. The system of claim 1, wherein each of the first and second monitoring devices further comprises sensors configured to monitor each of the first and second caregiver's vital data, sleep pattern data and activity data.

14. The system of claim 1, wherein the sensor system comprises wearable sensors configured to be worn by the user and to sense the user's vital data.

15. The system of claim 1, wherein the sensor system comprises a daytime wearable sensor and a nighttime wearable sensor and wherein the daytime wearable sensor and the nighttime wearable sensors are configured to be worn by the user and to sense the user's vital data during the day and during the night, respectively.

16. The system of claim 1, wherein the sensor system comprises skin attachable sensors configured to be attached to the user's skin and to sense the user's vital data.

17. The system of claim 1, wherein the sensor system comprises a microphone and a camera for capturing the sound and image data of the user, respectively.

18. The system of claim 1, wherein the sensor system is further configured to send an alarm notification to at least one of the first and second monitoring devices in cases when at least one of the collected data has a value above a predetermined threshold or out of a predetermined range.

19. The system of claim 1, wherein the sensor system is further configured to send an alarm notification to at least one of the first and second monitoring devices in cases when the user is about to or has moved away from the first location.

20. A method for monitoring a user comprising:
   collecting data comprising sound and image data of the user, a user's vital data, and ambient condition data, via a sensor system worn by the user and transmitting the collected data wirelessly to a transmitter positioned in a first location in a vicinity of the user;
   providing first and second monitoring devices configured to communicate wirelessly with the transmitter and to be worn by first and second caregivers of the user, respectively, wherein the first and second caregivers are located in a second location that is different from the first location;

providing a controller located in the second location and configured to communicate wirelessly with the first and second monitoring devices and the transmitter;

transmitting wirelessly live data feeds from the transmitter to the first and second monitoring devices and to the controller and wherein the live data feeds comprise the sound and image data of the user and the user's vital data;

providing and application and analyzing the live data feeds and determining whether any of the collected data has a value above a predetermined threshold or out of a predetermined range with the application and sending an alarm notification to at least one of the first and second monitoring devices in cases when at least one of the collected data has a value above the predetermined threshold or out of the predetermined range.

* * * * *